US008469916B2

(12) United States Patent
Wegener et al.

(10) Patent No.: US 8,469,916 B2
(45) Date of Patent: Jun. 25, 2013

(54) SYSTEMS AND METHODS FOR SINGLE NEEDLE CONTINUOUS PLASMA PROCESSING

(75) Inventors: Christopher J. Wegener, Libertyville, IL (US); Daniel R. Boggs, Libertyville, IL (US); Kyungyoon Min, Kildeer, IL (US); Prakash Mathew, Mukwonago, WI (US); Marc N. Weasler, West Bend, WI (US); Benjamin E. E. Kusters, Racine, WI (US)

(73) Assignee: Fenwal, Inc., Lake Zurich, IL (US)

(*) Notice: Subject to any disclaimer, the term of this patent is extended or adjusted under 35 U.S.C. 154(b) by 161 days.

(21) Appl. No.: 13/036,814

(22) Filed: Feb. 28, 2011

(65) Prior Publication Data

US 2012/0220915 A1 Aug. 30, 2012

(51) Int. Cl.
*A61M 37/00* (2006.01)
(52) U.S. Cl.
USPC ............. 604/6.04; 604/6.01; 210/87; 210/90; 210/324; 210/325; 210/630
(58) Field of Classification Search
USPC .................... 604/6.01, 6.04; 210/87, 90, 324, 210/325, 321.67, 630
See application file for complete search history.

(56) References Cited

U.S. PATENT DOCUMENTS

| | | | |
|---|---|---|---|
| 4,753,729 A | 6/1988 | Schoendorfer et al. | |
| 4,755,300 A | 7/1988 | Fischel et al. | |
| 4,776,964 A | 10/1988 | Schoendorfer et al. | |
| 4,790,942 A | 12/1988 | Shmidt et al. | |
| 4,851,126 A * | 7/1989 | Schoendorfer | 210/651 |
| 5,104,553 A * | 4/1992 | Lorenz et al. | 210/741 |
| 5,135,667 A | 8/1992 | Schoendorfer | |
| 5,194,145 A | 3/1993 | Schoendorfer | |
| 5,376,263 A | 12/1994 | Fischel | |
| 5,437,624 A * | 8/1995 | Langley | 604/6.05 |
| 6,099,730 A * | 8/2000 | Ameer et al. | 210/321.67 |
| 6,759,007 B1 * | 7/2004 | Westberg et al. | 422/44 |
| 6,811,707 B2 | 11/2004 | Rovatti et al. | |
| 7,108,672 B2 | 9/2006 | Steele et al. | |
| 7,220,354 B2 | 5/2007 | McLaughlin et al. | |
| 7,374,677 B2 * | 5/2008 | McLaughlin et al. | 210/321.67 |
| 7,695,423 B2 * | 4/2010 | Robinson et al. | 494/43 |
| 2002/0033370 A1 | 3/2002 | Bainbridge et al. | |
| 2004/0238445 A1 * | 12/2004 | McLaughlin et al. | 210/645 |
| 2008/0195025 A1 | 8/2008 | McLaughlin et al. | |
| 2009/0291819 A1 * | 11/2009 | Westberg et al. | 494/56 |

OTHER PUBLICATIONS

International Search Report and Written Opinion of the International Searching Authority for PCT Patent Application No. PCT/US12/26499, dated Jun. 6, 2012.

* cited by examiner

*Primary Examiner* — Tatyana Zalukaeva
*Assistant Examiner* — Ilya Treyger
(74) *Attorney, Agent, or Firm* — Cook Alex Ltd.

(57) ABSTRACT

Certain examples describe systems and methods for increasing plasma extracted from donor blood. An example method includes receiving blood extracted from a donor connected to a blood collection machine. The example method includes filtering the blood using a filtration device to remove at least a portion of plasma included in the blood to separate the plasma removed from remaining blood. The example method includes routing the plasma removed for collection. The example method includes re-filtering the remaining blood using a or the filtration device to remove additional plasma from the remaining blood. The example method includes routing the additional plasma removed for collection.

12 Claims, 13 Drawing Sheets

1500 → Red Cell Layer Limited Transport
The Concentration Polarization Model

1510

$$\frac{dQ_P}{dz} = \phi C k(z) \ln\left[\frac{H_W}{H_I}\left(1 - \frac{Q_P}{Q_I}\right)\right]$$

The mass transfer coefficient, *k*, varies from inlet to outlet and the cumulative plasma flow rate is obtained by integrating along the length, *z*, of the device.

1520

$$k(z) = M\left[\frac{R_R^{0.913} \omega^{3/2}}{G^{0.247} v^{1/2}}\right]$$

Inputs: Rotor radius, $R_R$; Gap, $G(z)$; Rotation speed, $\omega$; Blood viscosity, $v[H(z)]$

FIG. 15

# SYSTEMS AND METHODS FOR SINGLE NEEDLE CONTINUOUS PLASMA PROCESSING

FIELD

The present invention relates generally to methods, systems, and apparatus to provide blood processing from a donor. More particularly, the present invention relates to methods, systems, and apparatus to provide single needle continuous plasma collection from a donor.

BACKGROUND

By extracting only one or more components (e.g., red blood cells, platelets, and/or plasma) from a donor and returning remaining blood to the donor, a blood collection center can extract more of the component(s) from the donor than they could if only whole blood were collected.

BRIEF DESCRIPTION OF THE DRAWINGS

Certain example embodiments of the invention, together with features and the advantages thereof, may best be understood by reference to the following description taken in conjunction with the accompanying drawings, in which like reference numerals identify like elements in the figures, and in which:

FIG. 15 illustrates an example concentration polarization model formed for red cell layer limited transport.

Figure 1:
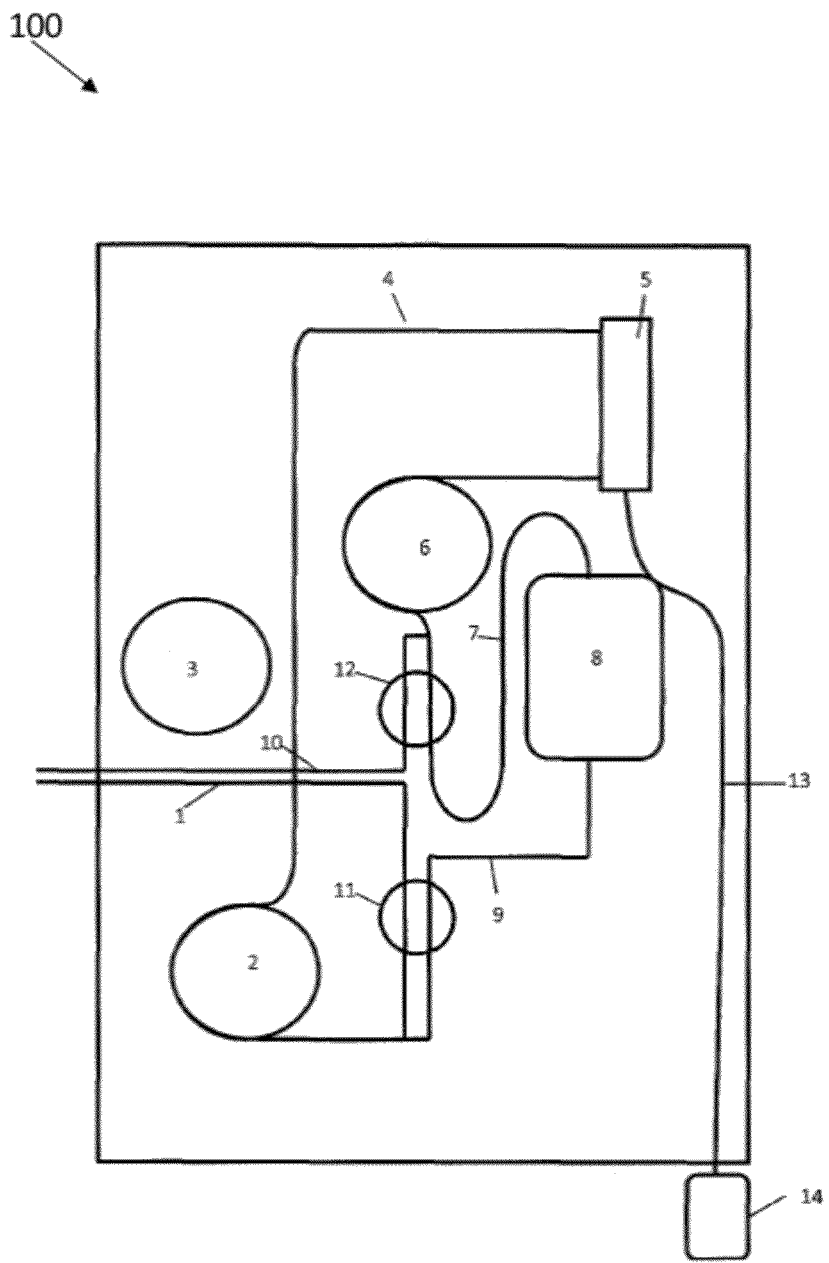
FIG. 1 illustrates an example collection apparatus configuration for plasmapheresis.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DESCRIPTION OF CERTAIN EXAMPLES

It will be understood that the present invention may be embodied in other specific forms without departing from the spirit thereof. The present examples and embodiments, therefore, are to be considered in all respects as illustrative and not restrictive, and the invention is not to be limited to the details presented herein.

Using a plasmacell (e.g., a Fenwal Plasmacell-C™) or other a blood filtering and plasma component separation device, plasma can be collected from blood drawn from a donor. The blood from the donor is directed into the plasmacell and filtered within the plasmacell to separate plasma from red blood cells and other blood component(s). In certain examples, a first time period is spent drawing blood from a donor for collection of the plasma component, and a second time period is spent returning remaining blood component(s) to the donor after a plasma collection draw cycle. In certain examples, rather than the plasmacell being idle during a return cycle, blood can be re-circulated or passed again through the plasmacell on return to collect additional plasma from the donor's blood before the blood remainder is returned to the donor.

Collection on return is based on a premise that, during a single needle procedure, blood separated by a spinning membrane separation device upon being drawn from a donor can be passed through and filtered by the same spinning membrane separation device a second time directly before being returned to a donor. Double filtering by the same spinning membrane separation device allows for continuous collection of plasma throughout the procedure, rather than allowing the separation device to be unutilized during a return of blood to the donor.

Certain examples allow for blood separation and plasma collection using a spinning membrane separation device while drawing and returning blood from a donor. That is, high hematocrit blood (e.g., 55-60%) is passed through a single separation device (e.g., a Fenwal Plasmacell™) for a second time before being returned to a donor during a return stage. In certain examples blood can be passed through a separation device in a forward and/or reverse direction. For example, pump and spinner direction can be reversed to allow blood flow into a bottom (e.g., a red blood cell port) and out of a top (e.g., a whole blood port) of the plasmacell. In certain examples, a plasmacell can be positioned upside down in the system for plasma separation and collection. In certain examples, blood is recirculated through a plasmacell in its original orientation.

Current practices allow blood separation and plasma collection using a plasmacell spinning membrane only while drawing blood from a donor. An ability to separate blood and collect plasma during the return phases of a procedure is advantageous because overall procedure time is significantly reduced. An ability to pass already concentrated blood from an in-process reservoir back through the plasmacell for a second time before being returned to a donor is a unique distinction between certain examples systems, apparatus, and methods described herein and prior plasmacell separation methods and practices. Prior practices return already concentrated blood straight back to the donor from the reservoir without passing the blood through the plasmacell for a second time, and, thus, do not continuously process blood throughout an entire procedure.

In certain examples, variations are based on a location at which blood is brought into the spinning membrane separation device during return. For example, blood can be removed from the in-process reservoir and separated by entering at the top of and exiting at the bottom of the plasmacell device, or in the reverse direction in which blood enters the bottom of the plasmacell and exits through the top. In another example, blood can enter and exit the plasmacell in the same direction as during blood collection.

In certain examples, plasma can be collected using a plasmapheresis device, such as Fenwal's Autopheresis-C™ instrument, which may be configured for continuous processing of blood and continuous collection of plasma during draw and return cycles, as well as during transition between cycles, all through a single needle. Thus, plasma can be filtered from donor blood with an almost zero transition time, as opposed to current techniques involving a single device that cycles and includes a transition time to prepare the device and the blood between each cycle.

Certain examples provide a method for plasma collection from a donor. The method includes receiving blood from a donor and filtering the received blood using a first separation filter. The method includes collecting, during a first time period, plasma separated from remaining blood components via the separation filter. The method includes re-filtering the remaining blood components through the first separation filter. The method includes collecting, during a second time period, plasma separated from remaining blood components via the separation filter. The method includes routing remaining blood components from the separation filter.

Certain examples provide a plasma collection system including a first plasma filtration device to filter plasma from blood drawn from a donor and a second plasma filtration device to filter plasma from blood drawn from a donor. The first plasma filtration device is adapted to receive blood from a donor and to filter a portion of plasma from the blood. The second plasma filtration device is adapted to receive blood remaining after filtration by the first plasma filtration device and to filter additional plasma from the blood remaining after filtration by the first plasma filtration device.

Certain examples provide a method for increasing plasma extracted from donor blood. The method includes receiving blood extracted from a donor connected to a blood collection machine. The method includes filtering the blood using a filtration device to remove at least a portion of plasma included in the blood to separate the plasma removed from remaining blood. The method includes routing the plasma removed for collection. The method includes re-filtering the remaining blood using the filtration device (or one or more connected filtration devices) to remove additional plasma from the remaining blood. The method includes routing the additional plasma removed for collection.

FIG. 1 illustrates an example collection apparatus configuration 100 for plasmapheresis. The example apparatus 100 includes a donor draw line 1, a blood pump (M2) 2, an anticoagulant (AC) pump (M1) 3, a continuous processing line 4, a separation device (e.g., Plasmacell-C) 5, a red cell pump (M3) 6, an in process line 7, an in process reservoir 8, a return processing line 9, a donor return line 10, binary clamps 11-12, a plasma line 13, and a plasma collection container 14. The system 100 is explained in further detail below in conjunction with a draw cycle configuration 200 and return cycle configuration 300.

Figure 2:
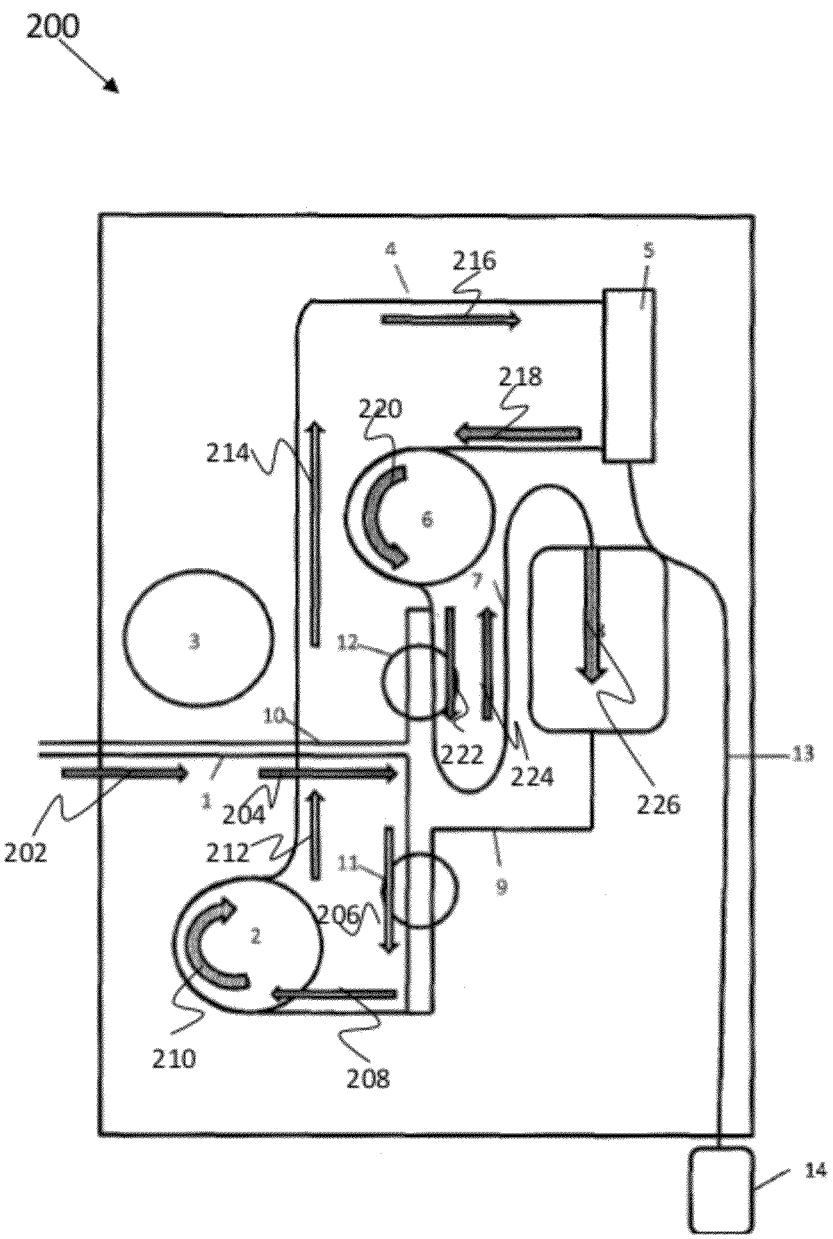
FIG. 2 illustrates an example draw cycle configuration in a collection-on-return apparatus.

FIG. 2 illustrates an example draw cycle configuration of a collection on return apparatus 200. The example apparatus 200 includes a donor draw line 1, a blood pump (M2) 2, an AC pump (M1) 3, a continuous processing line 4, a separation device 5, a red cell pump (M3) 6, an in process line 7, an in process reservoir 8, a return processing line 9, a donor return line 10, binary clamps 11-12, a plasma line 13, and a plasma collection container 14.

During a draw cycle 200, depicted in FIG. 2, as indicated by arrows 202, 204, 206, and 208, blood is continuously drawn into the system from a donor by the M2 blood pump 2 (as indicated by arrow 210) via the donor draw line 1. The donor draw line 1 is in an open position of the binary clamp 11 to allow blood flow while the return processing line 9 is in a closed position of the binary clamp 11 to prevent blood flow. As indicated by the flow of arrows 210, 212, 214, and 216, the M2 blood pump 2 passes the donor's whole blood (WB) through the continuous processing line 4 into the top port of the separation device 5. Within the separation device 5, the donor's WB is separated by a spinning membrane filtration device. Plasma is collected in the plasma collection container 14 via the plasma line 13 and, at 218, high hematocrit (HCT) blood (e.g., approximately 58% HCT) is pulled out of the separation device 5 by the M3 red cell pump 6 (as indicated by arrow 220) and, as indicated by arrows 222, 224, and 226, placed into the in process reservoir 8 via the in process line 7. The in process line 7 is in the open position of the binary clamp 12 to allow blood flow while the donor return line 9 is in the closed position of the binary clamp 12 to prevent blood flow. The draw cycle continues until the in process reservoir 8 is filled with high HCT blood. Once the in process reservoir 8 is filled, both binary clamps and/or other open/closing devices 11-12 are to instantaneously (or at least substantially instantaneously given some system delay) reverse their opened and closed positions to divert blood flow, allowing the system 200 to transition to a return cycle.

Figure 3:
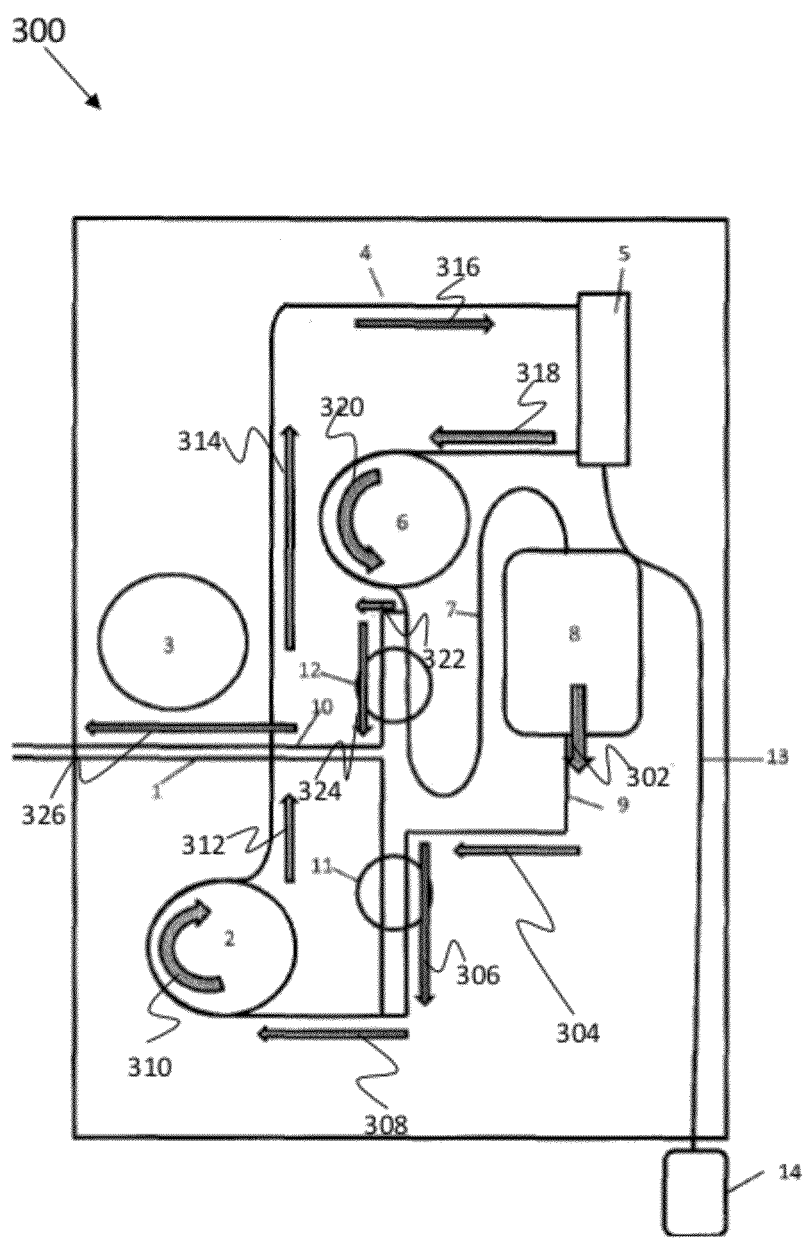
FIG. 3 illustrates an example return cycle configuration in a collection-on-return apparatus.

FIG. 3 illustrates an example return cycle configuration in a collection on return apparatus 300. The example apparatus 300 includes a donor draw line 1, a blood pump (M2) 2, an AC pump (M1) 3, a continuous processing line 4, a separation device 5, a red cell pump (M3) 6, an in process line 7, an in process reservoir 8, a return processing line 9, a donor return line 10, binary clamps 11-12, a plasma line 13, and a plasma collection container 14.

During a return cycle 300, depicted in the example of FIG. 3, high HCT blood is continuously (or at least substantially continuously accounting for some equipment delay) pumped out of the in-process reservoir 8, as indicated by arrows 302, 304, 306, and 308, by the M2 blood pump 2 via the return processing line 9. The return processing line 9 is in the open position of the binary clamp 11 to allow blood flow while the donor draw line 1 is in the closed position of the binary clamp 11 to prevent blood flow. As indicated by arrows 310, 312, 314, and 316, the M2 blood pump 2 passes the high HCT blood through the continuous processing line 4 into the top port of the separation device 5. Within the separation device 5, the high HCT blood is again separated by the spinning membrane filtration device. Plasma is collected in the plasma collection container 14 via the plasma line 13 and, as indicated by 318, concentrated red cells (e.g., approximately 68% HCT) are pulled out of the separation device 5 by the M3 red cell pump 6. As indicated by 320, 322, 324, and 326, the M3 red cell pump 6 then passes the concentrated red cells through the donor return line 10 and directly back to the donor. The donor return line 10 is opened to allow blood flow while the in-process line 7 is closed to prevent blood flow. The return cycle continues until the in process reservoir 8 is emptied. Once the in process reservoir 8 is emptied, both binary clamps 11-12 are to instantaneously (or at least substantially instantaneously) reverse their opened and closed positions to divert blood flow, allowing the system 300 to transition to a draw cycle. Transition draw and return cycles continue until the plasma collection target is met. Collecting plasma on both draw and return helps reduce system idle time and speed time of plasma collection from a donor. In certain examples, the first collection cycle begins on a draw and the last collection cycle ends on a return to help ensure excess blood does not remain in the system, for example.

In certain examples, by examining processing time and flow rate, a value or benefit of plasma collection on return as well as on draw can be evaluated. For example, a processing time for each draw-return cycle, $T_{PC}$, is given by $$T_{PC} = T_{DC} + T_{TC} + T_{RC} \quad (1)$$

where $T_{RC}$ is a return time, $T_{DC}$ is a draw time, and $T_{TC}$ is a collection-to-return transition time. Initially, ignoring $T_{TC}$ for the example and noting that $$T_{DC} = \frac{V_R}{Q_{R,IN}} \quad (2)$$

and $$T_{RC} = \frac{V_R}{Q_{R,OUT}},$$

where $V_R$ is a reservoir volume and $Q_{R,IN}$ and $Q_{R,OUT}$ are flow rates into and out of the reservoir, this becomes $$T_{PC} = V_R \left[ \frac{1}{Q_{R,IN}} + \frac{1}{Q_{R,OUT}} \right]. \quad (3)$$

An RBC flow rate into the reservoir, $Q_{R,IN}$, is given by $$Q_{R,IN} = Q_I - Q_{PD} \quad (4)$$

where $Q_I$ and $Q_{PD}$ are the inlet blood and plasma flow rates, respectively, during the draw. Thus, $$T_{PC} = V_R \left[ \frac{1}{Q_I - Q_{PD}} + \frac{1}{Q_{R,OUT}} \right]. \quad (5)$$

A volume of plasma collected per cycle, $V_{PC}$, is $$V_{PC} = Q_{PD} T_{DC} + Q_{PR} T_{RC} = V_R \left[ \frac{Q_{PD}}{Q_I - Q_P} + \frac{Q_{PR}}{Q_R} \right]. \quad (6)$$

A number of cycles, N, used to obtain a target amount of plasma, $V_T$, is $$N = \frac{V_T}{V_{PC}} \quad (7)$$

and a total processing time, $T_P$, is $$T_P = N T_{PC} = V_T \frac{T_{PC}}{V_{PC}}. \quad (8)$$

Combining Equations 5, 6, and 8 and simplifying yields $$T_P = \frac{V_T}{Q_{PD} + F Q_{PR}} [1 + F] \quad (9)$$

where $$F = \frac{Q_I - Q_{PD}}{Q_R}. \quad (10)$$

As shown in Equations 9 and 10, F indicates a ratio of reservoir filling rate to reservoir emptying rate. For a special case of $Q_{PR} = 0$, this becomes $$T_P = \frac{V_T}{Q_{PD}} [1 + F]. \quad (11)$$

Since N is not restricted to integer values, Equations 9 and 11 include a reduced contribution in the last fractional cycle.

Combining Equations 6 and 7, a number of cycles is given by $$N = \frac{V_T}{V_R} \cdot \frac{Q_I - Q_{PD}}{Q_{PD} + F Q_{PR}}. \quad (12)$$

A total transition time, $T_T$, is given by $$T_T = [int\ N + 1] T_{TC}, \quad (13)$$

where int N is an integer portion of N.

Thus, a total processing time, including transitions, is $$T_P = \frac{V_T}{Q_{PD} + F Q_{PR}} [1 + F] + [intN + 1] T_T, \quad (15)$$

where F and N are defined as above.

Figure 4:
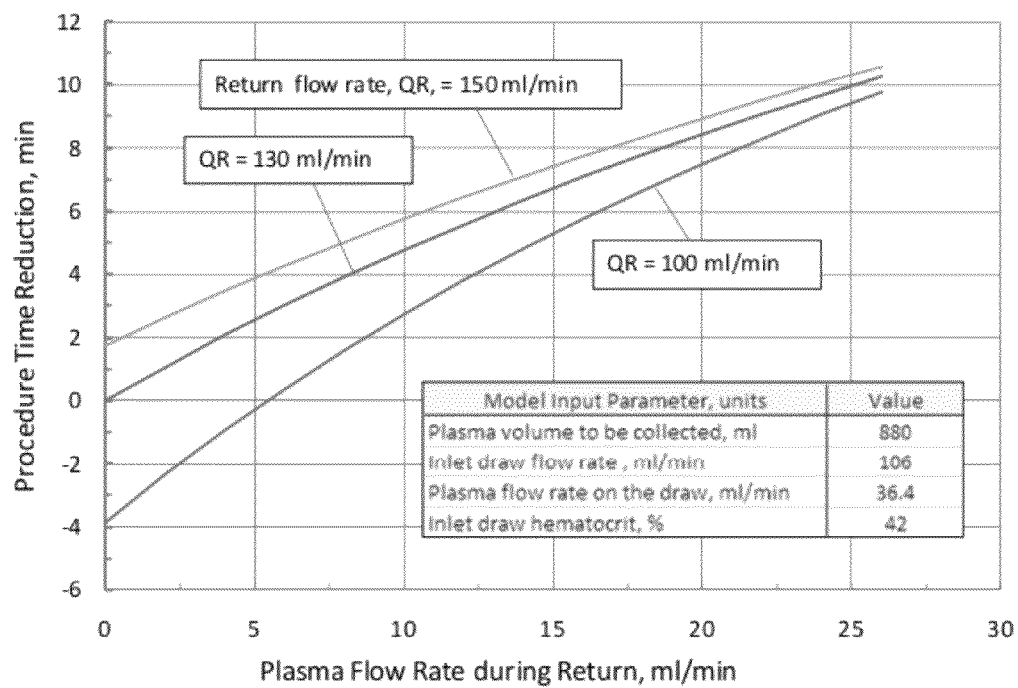
FIG. 4 depicts an example procedure time reduction as a function of return-phase plasma flow rate and blood flow rate.

A potential benefit of filtration during a return phase is illustrated for example draw-phase conditions in FIG. 4. FIG. 4 depicts a procedure time reduction (e.g., positive values) as a function of return-phase plasma flow rate and blood flow rate, for example. Plasma flow rate during return is expressed as a ratio of milliliters (ml) over minutes (min), for example. Procedure time reduction is expressed in minutes, for example.

Figure 5:
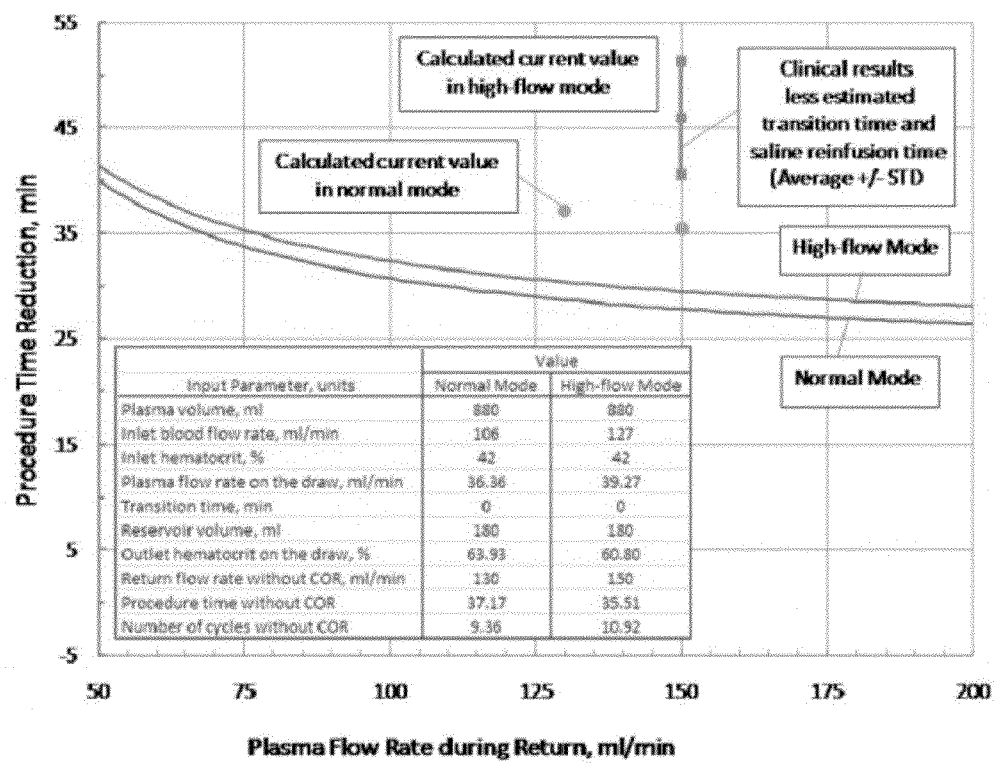
FIG. 5 shows an example effect of flow on processing time for both normal and turbo modes given performance according to a concentration polarization model with zero transition time.

In the example of FIG. 4, plasma flow rate on return has an upper bound at a concentration polarization (CP) limit. This upper limit can be estimated using a CP model. FIG. 5 shows an example effect of $Q_R$ on processing time for both normal and turbo modes given performance according to the CP model with zero transition time. Also shown are calculated processing times for normal and turbo modes without collection on return. Results from an example procedure time study are also shown for reference. As shown in the example of FIG. 5, a time savings of about nine minutes is expected with collection on return. Further, as shown in the example of FIG. 5, processing time is relatively insensitive to a return flow rate in a range of 130-150 milliliters per minute.

Figure 6:
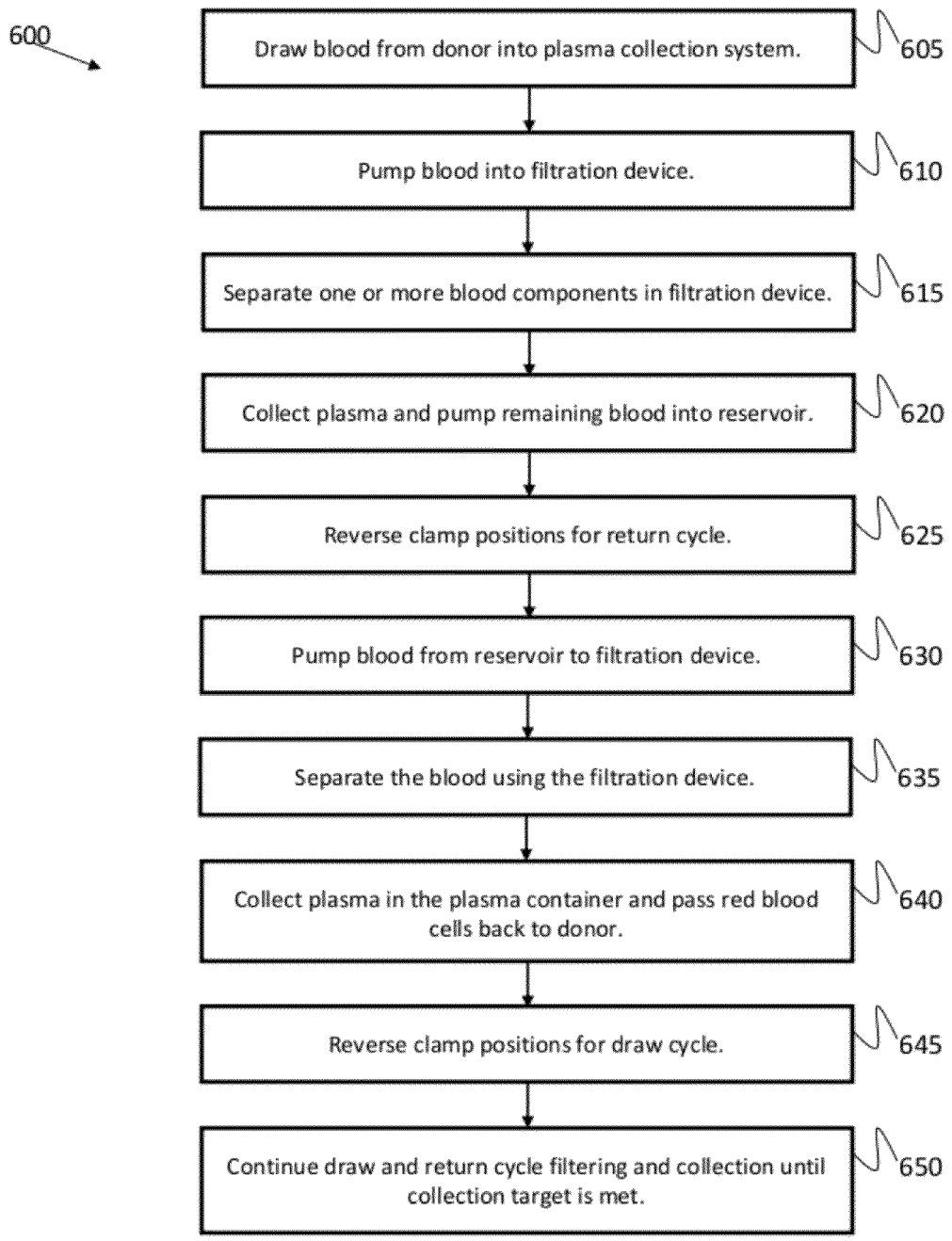
FIG. 6 depicts a flow diagram for an example method for plasma collection from a donor.

FIG. 6 depicts an example flow diagram representative of process(es) that may be used with respect to examples described herein. The example process(es) of FIG. 6 may be driven using a processor, a controller and/or any other suitable processing device. Although the example process(es) of FIG. 6 are described with reference to the flow diagram of FIG. 6, other methods of implementing the process(es) of FIG. 6 may be employed. For example, the order of execution of the blocks may be changed, and/or some of the blocks described may be changed, eliminated, sub-divided, or combined. Additionally, any or all of the example process(es) of FIG. 6 may be performed sequentially and/or in parallel.

FIG. 6 depicts a flow diagram for an example method 600 for plasma collection from a donor. At block 605, blood is drawn into a plasma and/or other blood component collection system from a donor using a pump to pull blood along a donor draw line. The donor draw line is placed in the open position with a first binary clamp to allow blood flow while a return processing line is closed using a second binary clamp to prevent blood flow through the return line. At block 610, the donor's whole blood (WB) is pumped into a spinning membrane filtration device (e.g., a plasmacell) through a top port of the filtration device. At block 615, within the spinning membrane filtration device, the donor's WB is separated by spinning and passing through one or more membrane filters. At block 620, plasma is collected in a plasma collection container or reservoir via a plasma line and remaining blood component(s) are pumped into an in process reservoir via an in process line. The in-process line is open to allow blood flow while a donor return line is closed to prevent blood flow through that line. The draw cycle of blocks 605-620 continues until the in process reservoir is filled with remaining blood.

At block 625, once the in process reservoir is filled, the clamp positions are reversed to divert blood flow, allowing the system to transition to a return cycle. At block 630, blood from the in-process reservoir is pumped out of the in process reservoir via the return processing line. The return processing line is open to allow blood flow while the donor draw line is closed to prevent blood flow. The blood is pumped into the top port of the spinning membrane filtration device. At block 635, within the spinning membrane filtration device, the blood is again separated by the spinning membrane filtration device. At block 640, plasma is collected in the plasma collection container via the plasma line 13 and concentrated red cells are pulled out of the filtration device by a pump and passed through the donor return line back to the donor. The donor return line is open to allow blood flow while the in process line is closed to prevent blood flow. The return cycle continues until the in process reservoir is emptied. At block 645, once the in process reservoir is emptied, the lines are to reverse their opened and closed positions (e.g., using binary clamps) to divert blood flow, allowing the system to transition to a draw cycle. At block 650, transition draw and return cycles continue until the plasma collection target is met.

Certain examples help increase plasmapheresis separation speed using a modular separation filter assembly. Currently, plasmapheresis filtration devices, such as the Autopheresis-C manufactured by Fenwal, separate plasma from whole blood using filtration technology. The separation speed (e.g., plasma production speed) is limited by a capacity of the filter assembly. Certain examples provide systems and methods to run a plasmapheresis procedure over multiple available instruments. For example, certain examples utilize a plasmapheresis device in conjunction with an identical (or substantially identical) second device (and/or a specialized spinner assembly) to increase separation throughput using a modular filtration assembly running on multiple instruments.

Using a second plasmapheresis device occupies that second device but increases speed of plasma separation from whole blood (e.g., by doubling the plasma separation speed). The modified kit is modularly expandable by just the filter assembly and does not require a whole second identical kit.

Certain examples can be extended from two instruments to two or more (multiple) instruments. Rather than using a second full featured instrument, the second instrument can include a motor spinner drive assembly only. The drive assembly can be modularly attached to a fully featured primary instrument. In certain examples, a kit and instrument can be modified so that the kit is extended in parallel and a second unused instrument is utilized as a slave device to effectively double the separation speed. In certain examples, the master or primary instrument can be retrofit with an add-on second instrument (e.g., a slave instrument). Certain examples can be extended to other apheresis processes and devices (e.g., in addition to plasmapheresis).

Figure 7:
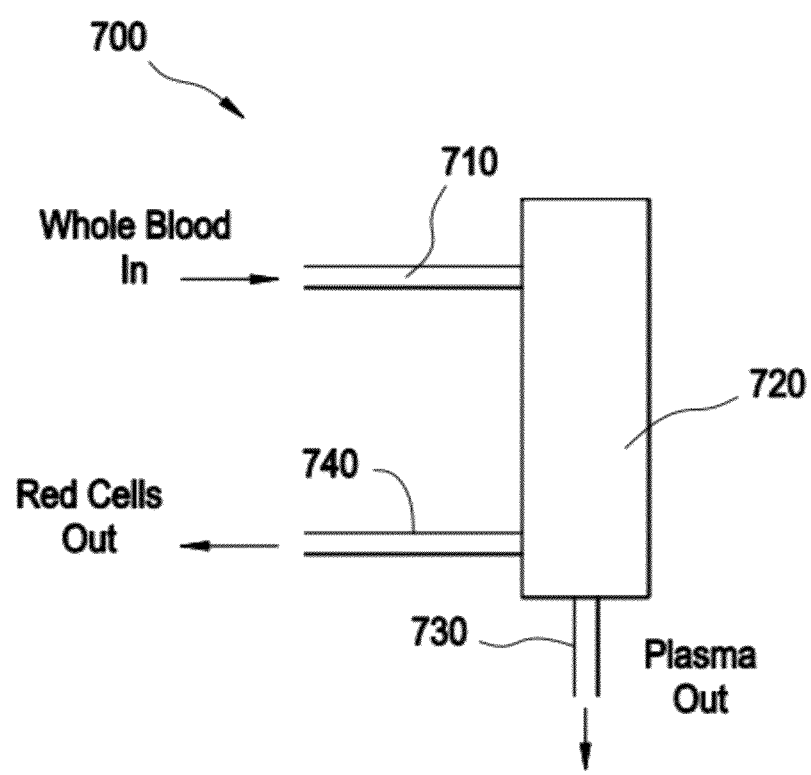
FIG. 7 shows an example three-port plasma separation filter device.

FIG. 7 shows an example three-port plasma separation filter device 700. Whole blood goes into the device 700 via a first port 710, where a spinning membrane inside a chamber 720 separates plasma from the cellular components. The chamber 720 outputs plasma via a second port 730 and red cell contents via a third port 740.

Figure 8:
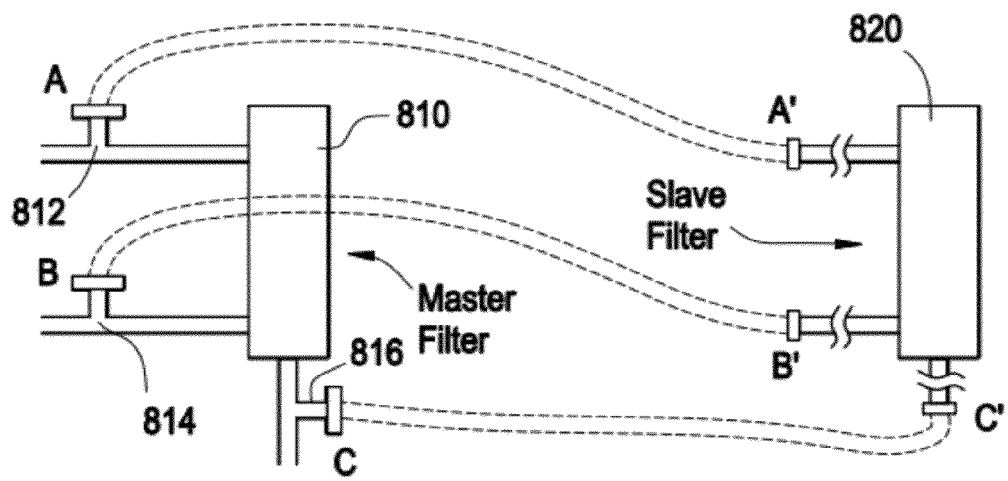
FIG. 8 shows example modifications to a standard separation device.

FIG. 8 shows example modifications to a "standard" separation device. The example new extensible kit is referred to as the "master" device 810 and is configured as a standard device with the exception of sealed-off Tees (A, B, C) at each of three ports 812, 814, 816. A "slave" device 820 of the example includes a filtration assembly only, which is capable of being connected to the master device 810 at the Tees using lengths of plastic tubing AA', BB', and CC'. The connections are quick-connect screw-on type connections, for example. Using master and slave devices 810, 815, an additional volume of plasma can be extracted from a single quantity or batch of blood drawn from a donor. Rather than processing the batch of blood once through the standard device, the batch of blood can be passed through the master device 810 and then through the slave device 820 to increase an amount of plasma separated and collected from the blood before it is returned to the donor, for example.

While the devices may be referred to as master and slave devices, in certain examples, the devices operate equally in parallel. In certain examples, the master device drives or controls operation in the slave device. Alternatively or in addition, the slave device can only include a portion of the components found in the master separation device sufficient to operate with the master device to filter blood.

Figure 9:
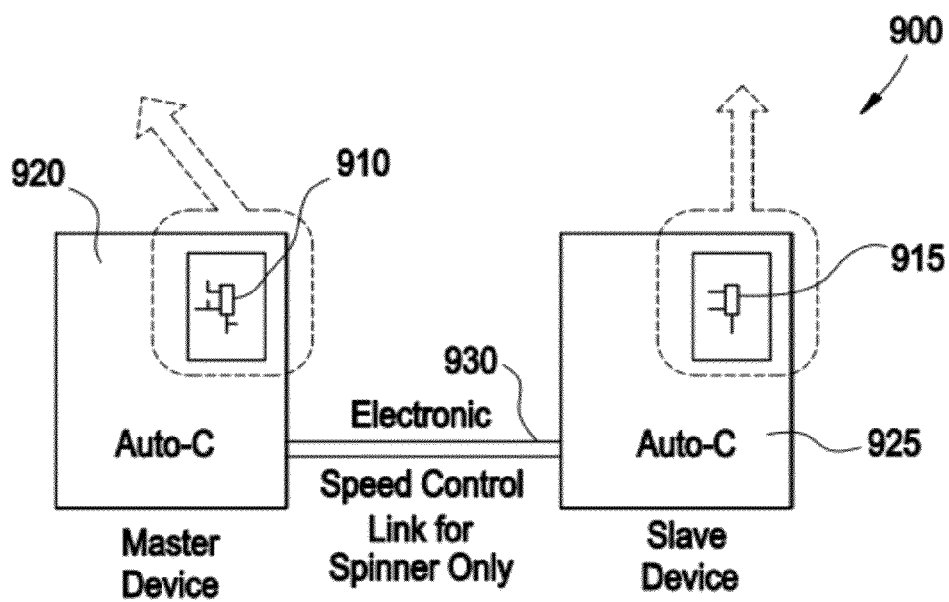
FIG. 9 shows example master and slave kits mounted in master and slave instruments.

FIG. 9 shows the master and slave devices 910, 915 mounted in master and slave instruments 920, 925. One device instrument 920 is designated the master device, and the master device 910 is mounted on that device instrument. The master device instrument 920 runs and controls a blood component collection procedure with a donor. The second instrument 925 is designated the slave and is powered on by and in close proximity to the master instrument 920. The slave unit 925 is connected to the master unit 920 via an electronic communication link which allows the master instrument 920 to control the speed of the filter/spinner assembly on the slave device 925 which then runs in a "slave" mode. The extension slave device 915 is mounted on the slave instrument 925, and tube(s) 930 are connected between the master device 910 and slave device 915.

The master-slave configuration 900 effectively allows for parallel separation to occur on both instruments simultaneously (or at least substantially simultaneously). Modifications can be made in the software running an instrument to account for tube lengths between the instruments for priming and device residual purposes. If a speed increase is not desired or necessary, the user can have the option of running just the master device on one single master instrument, with the Tees on the master device sterile capped off. In certain examples, the master-slave configuration 900 can be extended to include one or more slave units in conjunction with a primary instrument. The device filter assembly can be modularly expanded multiple times, for example.

In certain examples, rather than a full-featured secondary slave instrument, a special spinner drive motor assembly can be mechanically and electronically attached to the primary instrument to act as the slave device. The motor drive assembly can be a modular unit that can be plugged in and out of the primary device as needed or desired. In certain examples, one, two, or more of the slave motor drive units can be modularly attached to a single primary instrument to increase the processing speed multi-fold in conjunction with a multiply expanded kit. In certain examples, units can be connected by belts or gears based on a fixed speed ratio.

In certain examples, an Autopheresis-C disposable kit is modified such that the outlet of the original plasmacell separation device is connected to a second plasmacell separation device powered by a separate external spinner assembly.

Certain such example configurations can generate return hematocrits in excess of 80%. Previous tests had shown that a single plasmacell can generate return hematocrits of 65-70%. The increase in separation efficiency can reduce procedure times (e.g., up to eighteen minutes from Turbo field data) if implemented in the field.

An increase in available membrane surface area from arranging multiple plasmacells in series allows for increased separation efficiency. Alternatively or in addition, surface area can be doubled by creating a single plasmacell that is twice the length of the current device and/or by changing other dimension(s) of the plasmacell, for example.

In certain examples, turbulent mixing and/or cell rest period occurring in a length of tubing between linked plasmacells can be beneficial. In certain examples, a separation device can be redesigned to create additional turbulent mixing and/or rest periods to mimic this configuration. In certain examples, plasma collection port configurations can be implemented as separate entities and/or joined together.

Figure 10:
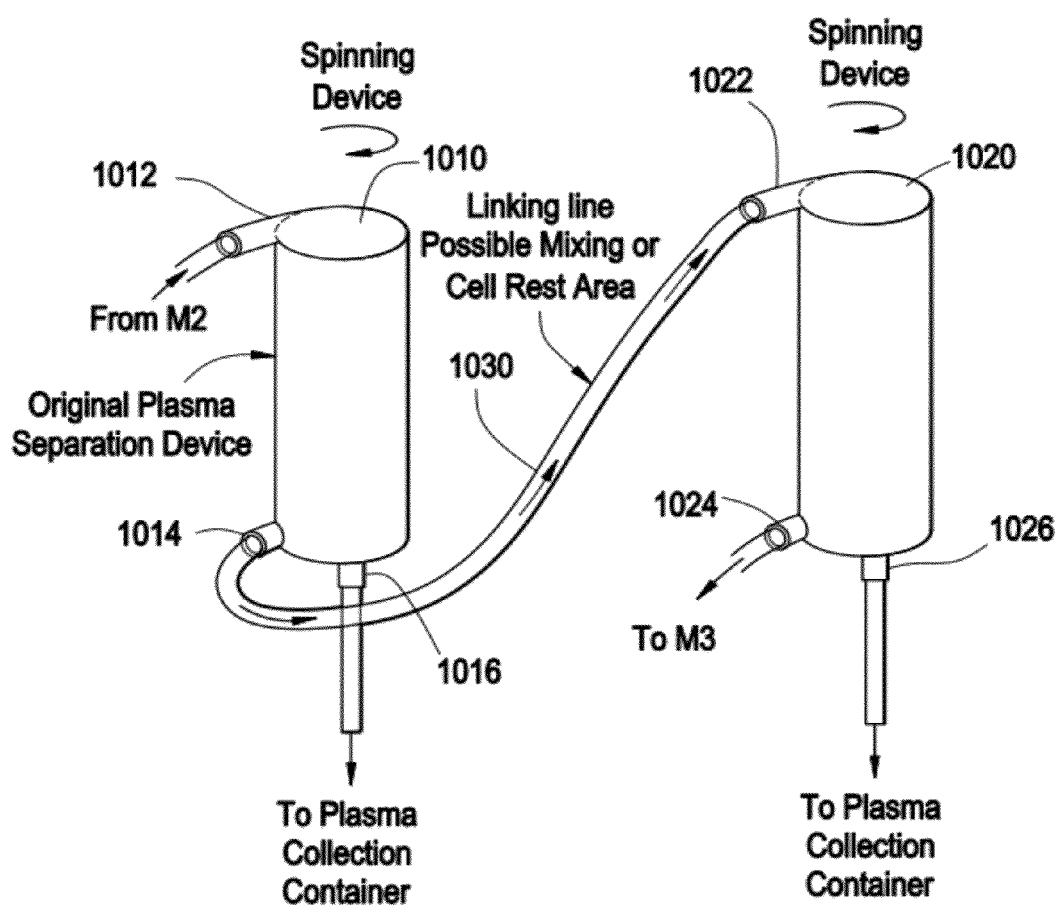
FIG. 10 illustrates two example Plasmacell-C separation devices linked in series.

In the example of FIG. 10, two plasmacell separation devices 1010, 1020 are linked in series. As shown in the example of FIG. 10, an inlet 1012 receives blood from a donor connected by a needle and line to the device 1010. The separation device 1010 separates at least some plasma from the remainder of the blood and provides plasma to a plasma container via an outlet 1016 and remaining blood through an outlet 1014. A tube 1030 routes the blood from the outlet 1014 to the second plasmacell separation device 1020. Blood enters the second separation device 1020 through an inlet 1022 and is separated into plasma and remaining component(s) in the device 1020. Additional collected plasma is routed to the plasma collection container via an outlet 1026, and remaining blood component(s) exit the device 1020 via an outlet 1024 to be returned to the donor.

When operating in series, a spinning speed of a second Plasmacell device can be adjusted based on one or more flow rates (e.g., red blood cell and/or plasma) from the first device. Red cells are fragile, and subjecting them to high shear can cause hemolysis. This risk for hemolysis generation increases with increasing blood viscosity (increasing hematocrit). In series, the second of the two separation devices can be spun at slower speed, reducing the risk of generating hemolysis in the higher hematocrit blood, for example.

Two linked plasmacells provide higher exit hematocrit than a single plasmacell, even when the rest of the disposable kit is identical (or substantially identical) to a single separation configuration. Hematocrit increases can be facilitated by increased surface area, cell rest period in a linking line (e.g., tube), mixing in the linking line, a combination of these factors, etc.

Figure 11:
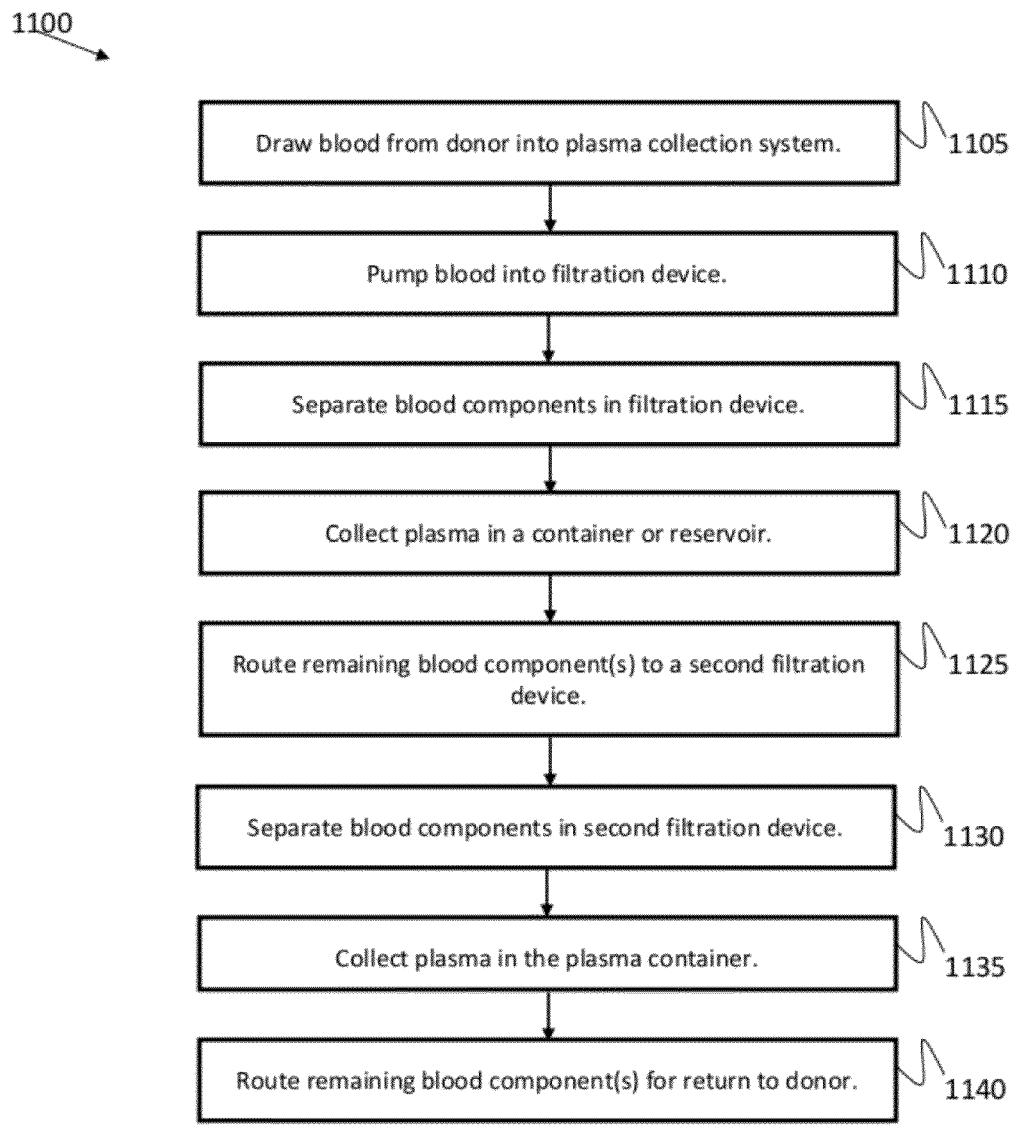
FIG. 11 depicts a flow diagram for an example method for plasma collection from a donor.

FIG. 11 depicts an example flow diagram representative of process(es) that may be used with respect to examples described herein. The example process(es) of FIG. 11 may be driven using a processor, a controller and/or any other suitable processing device. Although the example process(es) of FIG. 11 are described with reference to the flow diagram of FIG. 11, other methods of implementing the process(es) of FIG. 11 may be employed. For example, the order of execution of the blocks may be changed, and/or some of the blocks described may be changed, eliminated, sub-divided, or combined. Additionally, any or all of the example process(es) of FIG. 11 may be performed sequentially and/or in parallel.

FIG. 11 depicts a flow diagram for an example method 1100 for plasma collection from a donor. At block 1105, blood is drawn into a plasma and/or other blood component collection system from a donor using a pump to pull blood along a donor draw line. The donor draw line is placed in the open position with a first binary clamp to allow blood flow while a return processing line is closed using a second binary clamp to prevent blood flow through the return line. At block 1110, the donor's WB is pumped into a first spinning membrane filtration device (e.g., a plasmacell) through a top port of the filtration device. At block 1115, within the first spinning membrane filtration device, the donor's WB is separated by spinning and passing through one or more membrane filters. At block 1120, plasma is collected in a plasma collection container or reservoir.

At block 1125, remaining blood component(s) are routed to a second spinning membrane filtration device through an output port in the first spinning membrane filtration device. At block 1130, within the second spinning membrane filtration device, the remaining blood component(s) are separated by spinning and passing through one or more membrane filters. At block 1135, plasma is collected in a plasma collection container or reservoir. The plasma collection container/reservoir can be the same and/or a different container from that connected to the first spinning membrane filtration device, for example. At block 1140, remaining blood component(s) are routed from the second spinning membrane filtration device via an output port for return to the donor.

Figure 12:
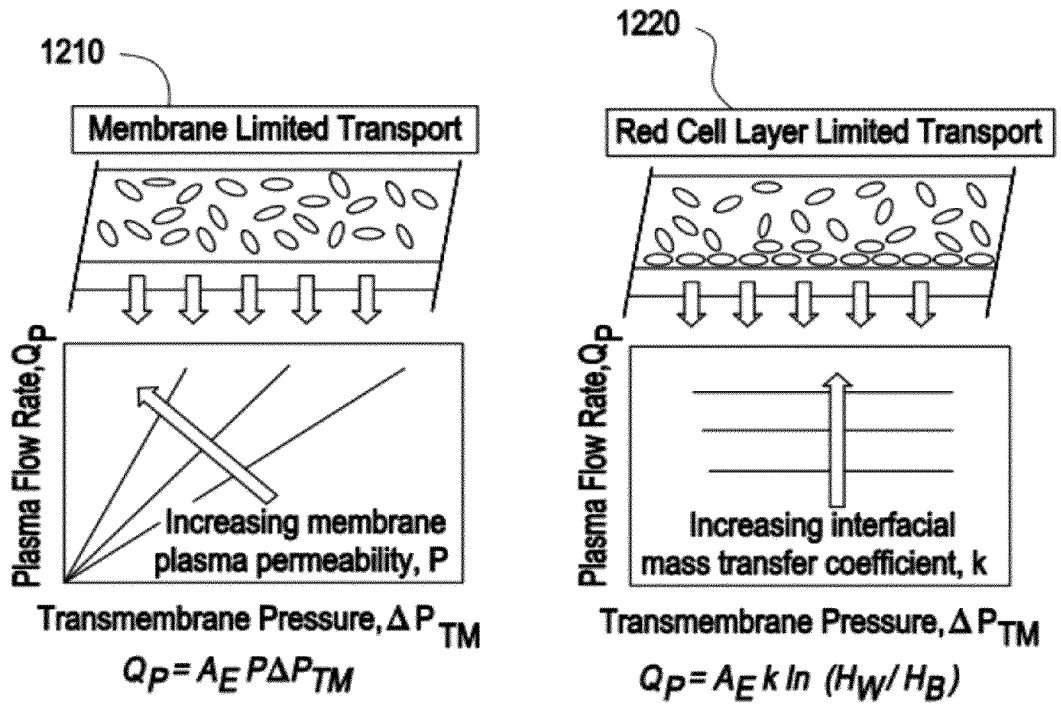
FIG. 12 shows an example comparison between membrane limited transport and red cell layer limited transport.

In the example of FIG. 12, membrane limited transport 1210 is compared with red cell layer limited transport 1220. A plasma flow rate, $Q_P$, is plotted against a transmembrane pressure, $\Delta P_{TM}$, for both membrane limited transport 1215 and red cell layer limited transport 1225. As shown in the example of FIG. 12, for membrane-limited transport, plasma flow rate increases with both increasing pressure and membrane permeability, P, whereas, with red-cell-layer limited transport, plasma flow rate is invariant with transmembrane pressure and increases with a mass transfer coefficient, k. For membrane limited transport, plasma flow rate can be calculated as follows:

$$Q_P = A_E P \Delta P_{TM} \quad (16)$$

where $A_E$ represents an effective membrane area.

For red cell layer limited transport, plasma flow rate ($Q_P$) can be calculated as follows:

$$Q_P = A_P k \ln(H_W/H_B), \quad (17)$$

where $H_W$ represents a wall hematocrit (or local hematocrit of the concentrated red cell solution adjacent to the membrane wall) and $H_B$ represents a local bulk fluid hematocrit away from the wall. $H_W$ is a function of the system/fluid. While the $H_W$ may not be truly known, it can be estimated to be near 90%, meaning that the remaining 10% plasma is not able to be forced from the system.

Figure 13:
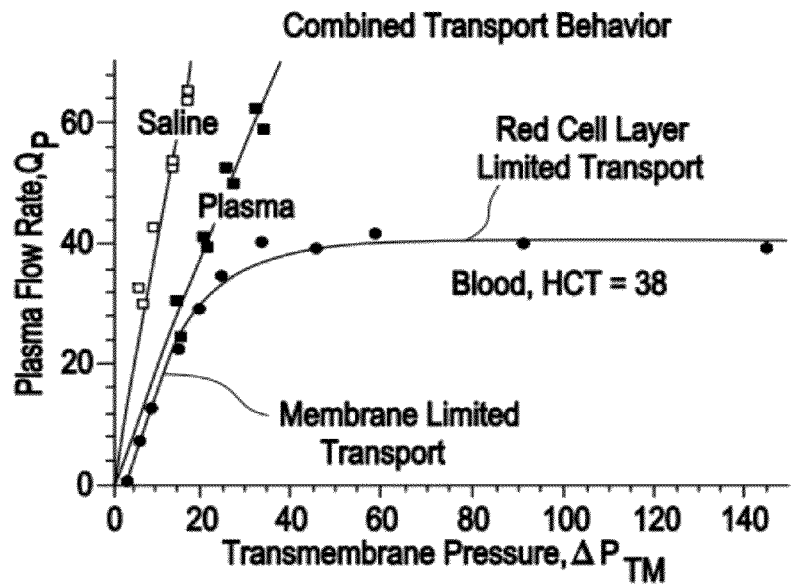
FIG. 13 depicts a combined transport behavior evaluated using both membrane limited transport and red cell layer limited transport.
Figure 14:
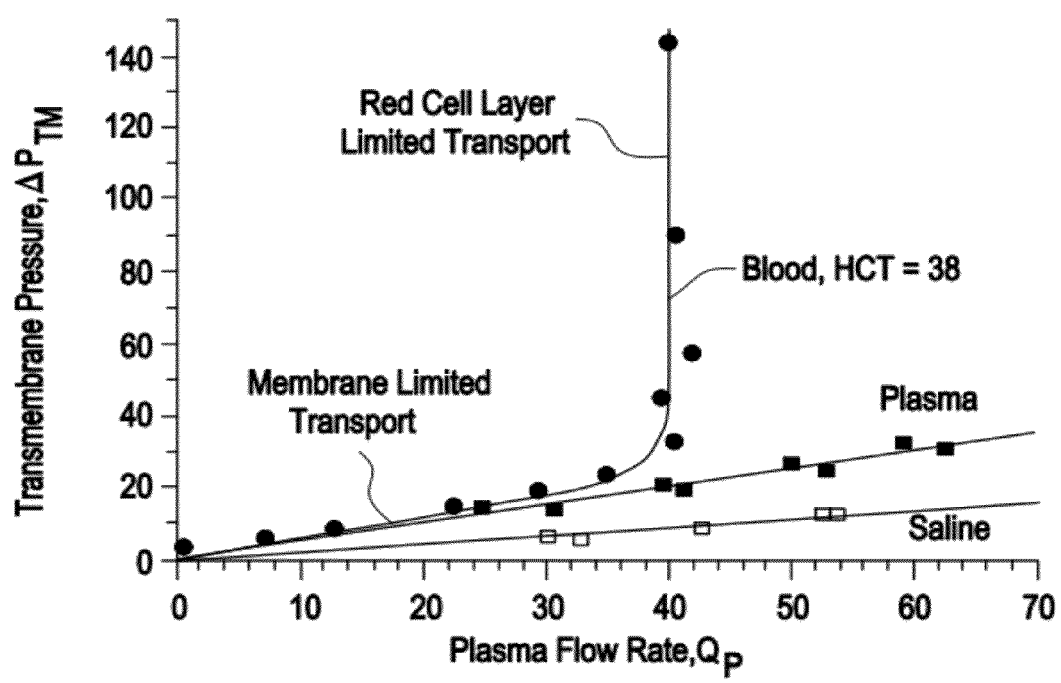
FIG. 14 illustrates an example graph of transmembrane pressure versus plasma flow rate.

As shown in the example of FIG. 13, a combined transport behavior can be evaluated using both membrane limited transport and red cell layer limited transport. Additionally, FIG. 14 illustrates an example graph of transmembrane pressure (TMP) versus plasma flow rate, where a collection device operates in a plasma demand mode with the pressure as a dependent variable. As a result, a concentration polarization model 1500 can be formed for red cell layer limited transport, as illustrated in the example of FIG. 15. Using the model 1500, a plasma flow rate 1510 can be determined as follows:

$$\frac{dQ_P}{dz} = \phi C k(z) \ln\left[\frac{H_W}{H_I}\left(1 - \frac{Q_P}{Q_I}\right)\right] \quad (18)$$

where $\phi$ is the fraction of membrane available for transport and C is the membrane circumference.

In the equation above, k varies from inlet to outlet, and the cumulative plasma flow rate is obtained by integrating along a length, z, of the device. As shown in FIG. 15, a determination 1520 of a mass transfer coefficient, k, for a device length, z, is determined using a rotation speed, w; a rotor radius, $R_R$; a gap, G(z); and a blood viscosity, v[H(z)]:

$$k(z) = M\left[\frac{R_R^{0.913} \omega^{3/2}}{G(z)^{0.247} v^{1/2}}\right]. \quad (19)$$

Thus, certain examples provide increased effective membrane area to increase device performance. Increased effective membrane area can be provided via collection of plasma both on draw and on return and/or by coupling multiple membrane filtration devices together in parallel and/or in series for blood filtration to remove and capture plasma before returning remaining blood components to a donor. Certain examples allow plasma filtering to continue without affect from transition times between cycles.

Although the forgoing discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

Certain examples can include processes that can be implemented using, for example, computer readable instructions that can be used to facilitate mobile blood applications for donors, operators, administrators, and/or providers. The example processes can be performed using a processor, a controller and/or any other suitable processing device. For example, the example processes can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes can be implemented using coded instructions (e.g., computer readable instructions) stored on a non-transitory computer readable medium such as a flash memory, a read-only memory (ROM), a random-access memory (RAM), a CD, a DVD, a Blu-ray, a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes can be implemented manually or as any combination(s) of any of the foregoing techniques, for example, any combination of firmware, software, discrete logic and/or hardware. Further, although example processes may be described with reference to a particular order and/or structure, other methods of implementing the processes may be employed. For example, the order of execution of the blocks can be changed, and/or some of the blocks described may be changed, eliminated, subdivided, or combined. Additionally, any or all of the example processes can be performed sequentially and/or in parallel by, for example, separate processing threads, processors, devices, discrete logic, circuits, etc.

While particular embodiments of the invention have been shown and described, it will be obvious to those skilled in the art that changes and modifications may be made therein without departing from the invention in its broader aspects.

The invention claimed is:

1. A blood processing method comprising:
   separating blood into a targeted component and a non-targeted component using a separation device;
   flowing out of the separation device, during a first time period, at least a portion of the targeted component separated from the non-targeted component via the separation device; and
   re-processing the non-targeted component to remove an additional amount of the same targeted component.

2. The method of claim 1, wherein said re-processing the non-targeted component includes using the separation device.

3. The method of claim 1, wherein said re-processing the non-targeted component includes using a second separation device.

4. The method of claim 3, wherein the separation device comprises a master separation device and the second separation device comprises a slave separation device.

5. The method of claim 3, wherein the separation devices are to operate in parallel.

6. The method of claim 1, wherein said flowing out of the separation device includes collecting at least a portion of the targeted component separated from the non-targeted component.

7. The method of claim 1, further comprising collecting, during a second time period, at least a portion of the additional amount of the same targeted component separated from the non-targeted component.

8. The method of claim 1, wherein said separating blood includes

- separating blood into targeted and non-targeted components using a separation device comprising a blood source draw line and a return processing line;
- opening the blood source draw line to allow blood flow through the blood source draw line while closing the return processing line to prevent blood flow through the return processing line during the first time period; and
- opening the return processing line to allow blood flow through the return processing line while closing the blood source draw line to prevent blood flow through the blood source draw line during a second time period.

9. The method of claim 1, wherein the targeted component is collected during first and second time periods alternating until a target volume is collected.

10. The method of claim 9, wherein target volume collection is completed during the second time period.

11. The method of claim 1, wherein said separating blood includes separating blood into targeted and non-targeted components using a separation device comprising a membrane filter.

12. The method of claim 1, wherein the targeted component comprises plasma and the non-targeted component comprises cellular blood components.

* * * * *